(12) United States Patent
Kato et al.

(10) Patent No.: US 11,504,501 B2
(45) Date of Patent: Nov. 22, 2022

(54) STEERABLE MEDICAL INSTRUMENT

(71) Applicants: CANON U.S.A., INC., Melville, NY (US); THE BRIGHAM AND WOMEN'S HOSPITAL INC., Boston, MA (US)

(72) Inventors: Takahisa Kato, Brookline, MA (US); Nobuhiko Hata, Newton, MA (US)

(73) Assignees: Canon U.S.A., Inc., Melville, NY (US); The Brigham and Women's Hospital, Inc., Boston, MA (US)

( * ) Notice: Subject to any disclaimer, the term of this patent is extended or adjusted under 35 U.S.C. 154(b) by 102 days.

(21) Appl. No.: 15/767,846

(22) PCT Filed: Oct. 12, 2016

(86) PCT No.: PCT/US2016/056546
§ 371 (c)(1),
(2) Date: Apr. 12, 2018

(87) PCT Pub. No.: WO2017/066253
PCT Pub. Date: Apr. 20, 2017

(65) Prior Publication Data
US 2018/0296800 A1  Oct. 18, 2018

Related U.S. Application Data

(60) Provisional application No. 62/241,995, filed on Oct. 15, 2015.

(51) Int. Cl.
*A61M 25/01* (2006.01)
*A61B 10/02* (2006.01)
*A61B 1/00* (2006.01)

(52) U.S. Cl.
CPC ..... *A61M 25/0147* (2013.01); *A61B 10/0233* (2013.01); *A61M 25/0138* (2013.01); *A61B 1/00154* (2013.01); *A61M 25/0136* (2013.01)

(58) Field of Classification Search
CPC .......... A61M 25/0147; A61M 25/0138; A61M 25/0013; A61M 25/0015; A61M 25/0004; A61B 1/00154
See application file for complete search history.

(56) References Cited

U.S. PATENT DOCUMENTS 4,686,963 A   8/1987 Cohen et al.
5,125,896 A   6/1992 Hojeibane
(Continued)

FOREIGN PATENT DOCUMENTS

EP   659387 A2   6/1995
EP   2289592 A2  3/2011
(Continued)

OTHER PUBLICATIONS

Chiang, L.S., et al, "Tendon Sheath Analysis for Estimation of Distal End Force and Elongation", IEEE/ASME International Conference on Advanced Intelligent Mechatroincs, Jul. 14-17, 2009, pp. 332-337.
(Continued)

*Primary Examiner* — Brandy S Lee
*Assistant Examiner* — Melissa A Snyder
(74) *Attorney, Agent, or Firm* — Canon U.S.A., Inc., IP Division

(57) ABSTRACT

The disclosure of this application relates generally to medical devices and in particular to a steerable medical instrument applicable to guide interventional tools and instruments, such as percutaneous biopsy and ablations tools and endoscopes. The steerable medical instrument has an outer and an inner tube where the inner tube is movable at the proximal end and fixed at the distal end. At least one of the outer tube and inner tube has a plurality of openings, which creates deformable portions so that the outer and the inner tubes can bend by moving the inner tube at the proximal end.

16 Claims, 6 Drawing Sheets

(56) References Cited

U.S. PATENT DOCUMENTS

| | | | |
|---|---|---|---|
| 5,469,254 | A | 11/1995 | Konomura |
| 6,858,005 | B2 | 2/2005 | Ohline et al. |
| 7,455,645 | B2 | 11/2008 | Goldenberg |
| 7,553,323 | B1 | 6/2009 | Perez et al. |
| 7,591,783 | B2 | 9/2009 | Boulais et al. |
| 7,731,667 | B2 | 6/2010 | Goldenberg |
| 7,785,252 | B2 | 8/2010 | Danitz et al. |
| 7,846,162 | B2 | 12/2010 | Nelson et al. |
| 8,125,755 | B2 | 2/2012 | Garcia et al. |
| 8,219,246 | B2 | 7/2012 | Buckingham et al. |
| 8,347,757 | B2 | 1/2013 | Duval |
| 8,348,861 | B2 | 1/2013 | Glozman et al. |
| 8,388,519 | B2 | 3/2013 | Garcia et al. |
| 8,394,054 | B2 | 3/2013 | Wallace et al. |
| 8,403,833 | B2 | 3/2013 | Umemoto |
| 8,424,941 | B2 | 4/2013 | Ihrke et al. |
| 8,578,810 | B2 | 11/2013 | Donhowe |
| 8,915,841 | B2 | 12/2014 | Naito |
| 9,144,370 | B2 | 9/2015 | Kato et al. |
| 2003/0045778 | A1 | 3/2003 | Ohline et al. |
| 2004/0138525 | A1 | 7/2004 | Saddat et al. |
| 2005/0131279 | A1 | 6/2005 | Boulais et al. |
| 2007/0142744 | A1 | 6/2007 | Provencher |
| 2007/0219581 | A1 | 9/2007 | Dohi et al. |
| 2008/0039715 | A1 | 2/2008 | Wilson et al. |
| 2008/0147158 | A1 | 6/2008 | Zweber et al. |
| 2008/0221592 | A1 | 9/2008 | Kawai |
| 2008/0281293 | A1 | 11/2008 | Peh et al. |
| 2008/0287741 | A1 | 11/2008 | Ostrovsky et al. |
| 2009/0095112 | A1 | 4/2009 | Buckingham et al. |
| 2010/0010298 | A1 | 1/2010 | Bakos et al. |
| 2011/0196199 | A1 | 8/2011 | Donhowe et al. |
| 2011/0224688 | A1 | 9/2011 | Larkin et al. |
| 2011/0251519 | A1 | 10/2011 | Romoscanu |
| 2011/0257480 | A1 | 10/2011 | Takahashi et al. |
| 2011/0270170 | A1 | 11/2011 | Gardeski et al. |
| 2012/0046522 | A1 | 2/2012 | Naito |
| 2012/0065628 | A1 | 3/2012 | Naito |
| 2012/0071752 | A1 | 3/2012 | Sewell et al. |
| 2012/0078053 | A1 | 3/2012 | Phee et al. |
| 2012/0136381 | A1* | 5/2012 | Morrison ........... A61B 17/3417 606/185 |
| 2012/0179146 | A1 | 7/2012 | Fan et al. |
| 2012/0203142 | A1 | 8/2012 | Bedell |
| 2012/0271109 | A1 | 10/2012 | Belson |
| 2013/0085333 | A1 | 4/2013 | Ramamurthy et al. |
| 2013/0090763 | A1 | 4/2013 | Simaan et al. |
| 2013/0197539 | A1 | 8/2013 | Simaan et al. |
| 2013/0225996 | A1 | 8/2013 | Dillard et al. |
| 2013/0231679 | A1 | 9/2013 | Wallace et al. |
| 2013/0303897 | A1 | 11/2013 | Pursely |
| 2013/0304034 | A1* | 11/2013 | Cabiri ............... A61M 25/0138 604/528 |
| 2014/0243592 | A1 | 8/2014 | Kato et al. |
| 2014/0350462 | A1 | 11/2014 | Ataollahi |
| 2015/0088161 | A1 | 3/2015 | Hata et al. |
| 2017/0304014 | A1 | 10/2017 | Au et al. |

FOREIGN PATENT DOCUMENTS

| | | | |
|---|---|---|---|
| EP | 2289592 | A3 | 11/2011 |
| JP | 2005533594 | A | 11/2005 |
| WO | 2007/141784 | A2 | 12/2007 |
| WO | 2017/003468 | A1 | 1/2017 |

OTHER PUBLICATIONS

Yoon, H., et al, "Active Bending Endoscopy Robot System for Navigation through Sinus Area", IEEE/RSJ International Conference on Intelligent Robots and Systems, Sep. 25-30, 2011, pp. 967-972.

Kato, T. et al, "Multi-section continuum robot for endoscopic surgical clipping of intracranial aneurysms", Med Image Comput Comput Assist Interv., 2013, pp. 364-371, vol. 16, No. 0 1.

Weiss, J.A., et al, "Computational Modeling of Ligament Mechanics", Critical Reviews™ in Biomedical Engineering, 2001, pp. 1-70, vol. 29, No. 4.

Webster, R. J. et al, "Design and Kinematic Modeling of Constant Curvature Continuum Robots: A Review", The International Journal of Robotics Research, 2010, pp. 1661-1683, vol. 29, No. 13.

Yoshimitsu, K. et al, "A novel four-wire-driven robotic catheter for radio-frequency ablation treatment", Int J Comput Assist Radiol Surg., Sep. 2014, pp. 867-874, vol. 9, No. 5.

Gupta, S. et al, "Using a Coaxial Technique with a Curved Inner Needle for CT-Guided Fine-Needle Aspirationb Biopsy", Technical Innovation, AJR:179, Jul. 2002, pp. 109-112.

Singh, A.K., et al, "Core Biopsy with Curved Needle Technique", Vascular and Interventional Radiology, Clinical Observations, AJR:191, Dec. 2008, pp. 1745-1750.

Phee, S.J., et al, "Tendon sheath analysis for estimation of distal end force and enlongation for sensorless distal end", Robotics, 2010, Cambridge University Press.

Butler, E. J., et al, "Robotic Neuro-Endoscope with Concentric Tube Augmentation", IEEE/RSJ International Conference on Intelligent Robots and Systems, Oct. 7-12, 2012, pp. 2941-2946.

Camarillo, D.B., et al, "Configuration Tracking for Contiuum Manipulators with Coupled Tendon Drive", IEEE Transactions on Robotics, Aug. 2009, pp. 798-808, vol. 25, No. 4, with Abstract.

* cited by examiner

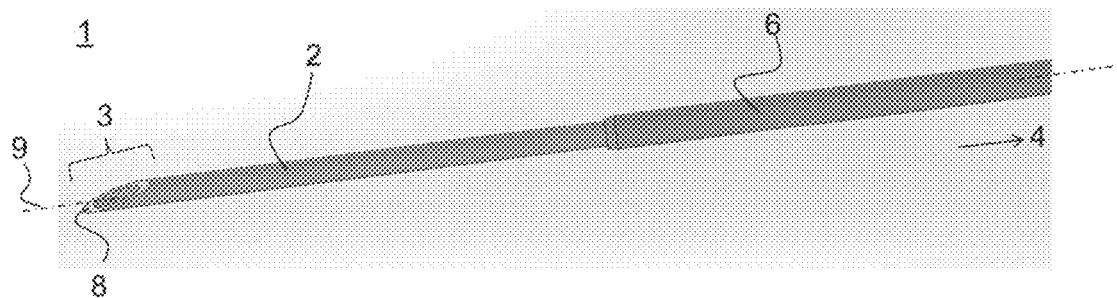
FIG.1a
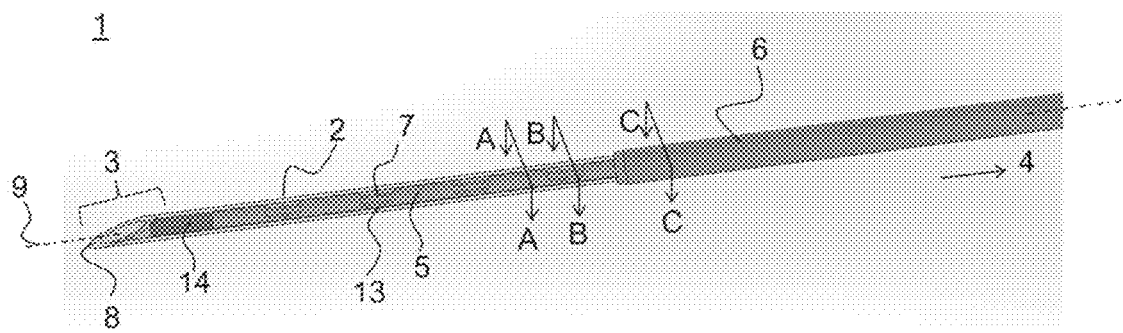
FIG.1b
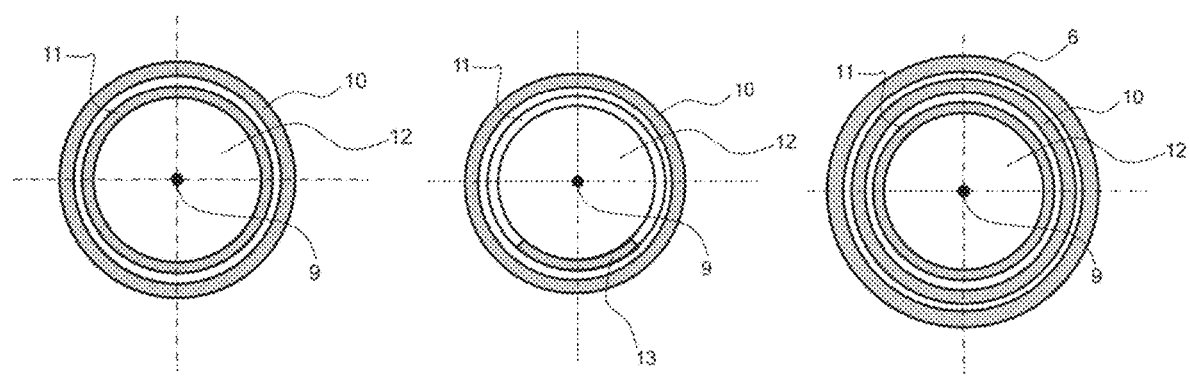
Cross Section A-A
FIG.2a
Cross Section B-B
FIG.2b
Cross Section C-C
FIG.2c Cross Section H-H Cross Section I-I Cross Section J-J

STEERABLE MEDICAL INSTRUMENT

CROSS-REFERENCE TO RELATED APPLICATIONS

This application is a national stage application of PCT/US16/56546 filed 12 Oct. 2016 and claims priority from Provisional Application No. 62/241,995 filed 15 Oct. 2015 the disclosures of each of which are hereby incorporated by reference herein in their entirety.

FIELD OF THE INVENTION

This application relates generally to medical devices and in particular to medical devices for percutaneous interventional procedures.

BACKGROUND

As the medical profession continues to look for techniques that are less invasive, the need for minimally invasive, percutaneous devices increases. However, there is often limited control over these percutaneous devices after insertion in the patient skin. Often, the instruments can be controlled to define insertion depth, but insertion directions cannot be changed without repetition of difficult needle placements or punctures through the skin, pleura and peritoneum.

Moreover, although the shortest trajectory between the skin and the target lesion, i.e. a straight trajectory, is preferred, this trajectory is not always possible because of intervening structures such as bowel loops, bones, major blood vessels, or lungs. Thus, when the instrument placement is not in line with the target lesions, the options include repositioning of the needle or use of a curved needle. For example, a curved-fine-needle aspiration and curved core biopsy needle have been used. See, for example, Singh, A. K., et al., AJR: 191, December, 2008, pp1745-1750. A curved needle can be used to avoid penetrating the interposed structure. See, for example, Gupta S., et al., AJR:179, July 2002, pp109-112.

However, the curved needle has only passive (fixed) curvature. Therefore, the procedure with the curved needle is still limited to control of the instrument placement to aim the target lesions from suboptimal needle placements or to avoid the interposed structure.

To improve this issue, different techniques of active steerable devices have been disclosed. U.S. Pat. Pub. 2012/0136381 provides actively variable curvature of the instrument by combining stationary hollow part with movable inner rod. The inner rod pulls the tip of the stationary hollow part and bends the entire structure. WO 2007/141784 provides steering capability for the standard needle by using base manipulation. The needle is mounted on the robotic insertion unit and is subjected to lateral steering force from the robotic insertion unit. The lateral steering force can steer the needle to opposite direction of this lateral steering force.

However, these active steerable devices still have numerous limitations. For example, the active steerable instrument in U.S. Pat. Pub. 2012/0136381A1 does not have a channel in the instruments. The device includes a hollow outer tube, named a transducer, which needs to be removed after deployment of the transducer to perform interventional procedures. Therefore the procedure becomes more cumbersome with this device. Also, in the case of the cured biopsy needle with the transducer, physician can access multiple target lesions with the same transducer location by changing the pre fixed curvatures of multiple needles. But this device cannot perform this procedure because of lack of channels.

Moreover, the bending stiffness between the stationary hollow part and the inner rod are not identical. This may cause large mechanical interaction between these two parts and increase driving force for bending. Therefore the device including handle parts is difficult to be miniaturized and to be robust from fractures at the fixing tip of movable inner rod.

The active steerable instrument in WO 2007/141784A2 has limitation of steerability over the insertion depth. The lateral force from outside of the skin is not transmitted well to the needle in deep position because the needle is mechanically constrained from the anatomy. Suboptimal placement of needle will occur more and more when the insertion depth is deer. Therefore, the instrument will not work well in the case physician needs to adjust the needle directions.

Also, to get the needle bend, the lateral force needs to be transduced to bending moment via the mechanical interaction between the needle and the anatomy. This may include uncertainty of bending moment because the mechanical property of the anatomy is inhomogeneous and will vary between patients.

Moreover, to bend the needle, the insertion unit needs to have a large stroke of angulation or translation to generate enough lateral force. This makes the instrument large and difficult to miniaturize. Also this makes manual steering with this instrument difficult and unrealistic.

Thus, there is provided a medical instrument that overcomes the limitations as discussed above.

SUMMARY

According to at least one embodiment of the invention, there is a steerable medical instrument. This instrument comprises an outer tube having a centroid along longitudinal direction and having a proximal and a distal end; and an inner tube having a centroid along longitudinal direction, which is surrounded by the outer tube. In this steerable medical instrument, the inner tube is movable along the direction of the centroid at the proximal end, and the inner tube is fixed at the distal end to the outer tube. At least one of the outer- and the inner-tubes have a plurality of openings, which creates effective deformable portions with offset from the centroid so that the outer and the inner tubes can bend by moving the inner tube at the proximal end. Alternatively or additionally, the outer and the inner tubes can bend by moving the outer tube at the proximal end. The plurality of openings may be on the inner tube, the outer tube, or both the inner tube and the outer tube. In some embodiments, there is provided a device having an outer tube and an inner tube as described herein which is a bendable tubular body, but not necessarily a medical instrument. Each of the additions described herein for a steerable medical instrument is also contemplated in a bendable tubular body.

In some embodiments, the steerable medical instrument or other bendable tubular body has less torsional motion than comparable instruments without the plurality of openings and deformable portions.

Thus, there is provided a steerable medical instrument that has, for example, bidirectional steering control using push and pull manipulation.

BRIEF DESCRIPTION OF DRAWINGS

Further objects, features and advantages of the present invention will become apparent from the following detailed description when taken in conjunction with the accompanying Figures showing illustrative embodiments of the present invention.

FIGS. 1a and 1b are illustrations of an exemplary steerable medical instrument to a first embodiment of the present invention. FIG. 1b shows the same device as FIG. 1a but with a transparent outer tube 2.

FIGS. 2a, 2b, and 2c show cross sections A-A (FIG. 2a), B-B(FIG. 2b), and C-C (FIG. 2c) as shown in FIG. 1b.

FIG. 3a shows a driving tensile force D and FIG. 3b shows a driving compression force D'.

FIG. 4b shows the same device as FIG. 4a but with a transparent outer tube 2. FIG. 4c shows the tip of the same device in a bent configuration.

FIG. 6a shows a side view of an exemplary steerable medical instrument. FIGS. 6b and 6c are close-up views of the box L with dotted lines.

FIGS. 7a and 7b are images of an exemplary steerable medical instrument, wherein FIG. 7b is a close-up view of the box M with dotted lines and with the addition of a dime for sizing.

DETAILED DESCRIPTION

Figure 3A:
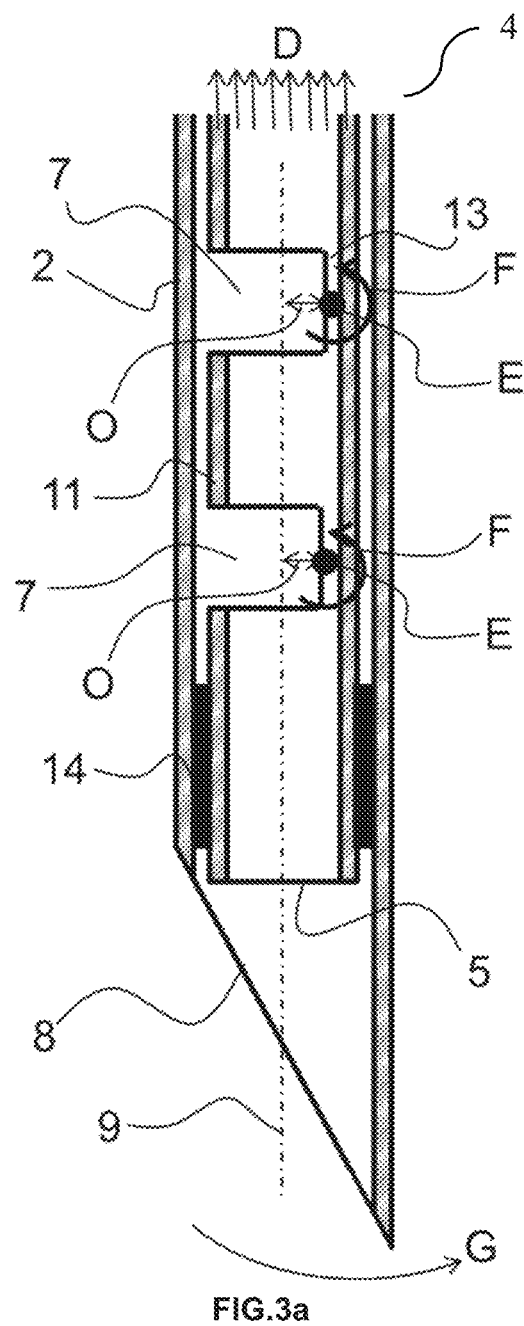
FIGS. 3a and 3b are the cross sectional view of an exemplary steerable medical instrument at the distal end.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure.

Embodiment 1

FIGS. 1a and 1b are illustrations of an exemplary steerable medical instrument to a first embodiment of the present invention. The medical instrument 1 comprises an outer tube 2, an inner tube 5 and an introducer 6. Specifically FIG. 1b shows inside of the outer tube 2 by using transparent color for the outer tube 2.

The medical steerable instrument 1 shown in this embodiment includes a distal end 3, a proximal end 4 and a centroid 9 and extends along the centroid 9. The outer tube 2, the inner tube 5 and the introducer 6 deploy while sharing the same centroid 9. The outer tube 2 includes a beveled tip 8 at the distal end 3 and is surrounded by the introducer 6. The outer tube 2 is not fixed on the introducer 6. Therefore position of the outer tube 2 can be adjustable along the centroid 9.

The steerable medical instrument can be inserted puncturing the skin with the beveled tip 8. The inner tube 5 locates in the outer tube 2 and is fix or attached to the outer tube 2 by an attachment portion 14 that is located at the distal end of the outer tube 2. The rest of the inner tube 5 from attaching spot with the attachment portion 14 is free to move against the outer tube 2. The attachment portion 14 may be a direct connection between the two tube or it may comprise one or more spacer elements that fix the tubes together.

The steerable medical instrument 1 as described in this embodiment may include two handles on the proximal end 4 that are not shown in figures. One of the two handles connects to the introducer 6, and the other includes the outer tube 2 and the inner tube 5. The outer tube 2 is fixed on the handle. Also the inner tube 5 is supported by movable parts of the handle so that operators can control position of the inner tube 5 over the direction of centroid 9. Two handles is detachable each other so that the transducer 6 can be separated from the outer tube 2 and the inner tube 5.

As shown in FIG. 1b, the inner tube 5 includes four openings 7. The opening 7 creates a deformable portion 13. In this particular embodiment, these four openings 7 create four deformable portions 13 along direction of centroid 9. These deformable portions 13 together form a serial bending spring system putting rigid portions, i.e. the parts of inner tube without openings 7, between these deformable portions 13. The amount of deformability created by the deformable portions can vary based on how much bend is needed in the device and can be modified by the size, shape, and number of deformable portions compared to openings as well as the material used.

While this embodiment provides four openings 7, the number of opening is not limiting—the inner tube 5 may include 1, 2, 3, 4, 5, 6, 7, 8, 9, 10, 11, 12 or more openings. A greater number of openings is preferred in embodiments where the steerable medical instrument is longer or where a higher degree of flexibility is required. The plurality of openings can be formed in such a way and in such a number so as to limit torsional motion of the steerable medical instrument. For example, torsional motion can be reduced substantially compared to the torsional motion of a steerable medical instrument not having opening with, for example, a key portion. In some embodiments the torsional motion is release by more than half compared to a steerable medical instrument not having opening.

FIGS. 2a, 2b, 2c show cross sections A-A, B-B and C-C of FIG. 1b. On position of the rigid portions on the inner tube 2, the outer tube 10 and the inner tube 11 surround a channel 12 (cross sections A-A, FIG. 2a). On position of the openings 7 (deformable portions 13), the outer tube 10 surround the channel 12 and isolate the channel 12 from outside of the outer tube 2. The deformable portion 13 comprises effective leaf spring with an arc shaped cross section. The deformable portion 13 locates with offset from the centroid 9. On position of the introducer 6, the introducer 6, the outer tube 10 and the inner tube 11 surround the channel 12 and locate with the same centroid 9. Through all longitudinal direction of the steerable medical instrument 1, the channel 12 is isolated from outside of the steerable medical instrument 1. Therefore the channel 12 can, for example, guide the interventional tools or can transport liquids and air between the distal end 3 and the proximal end 4.

Figure 3B:
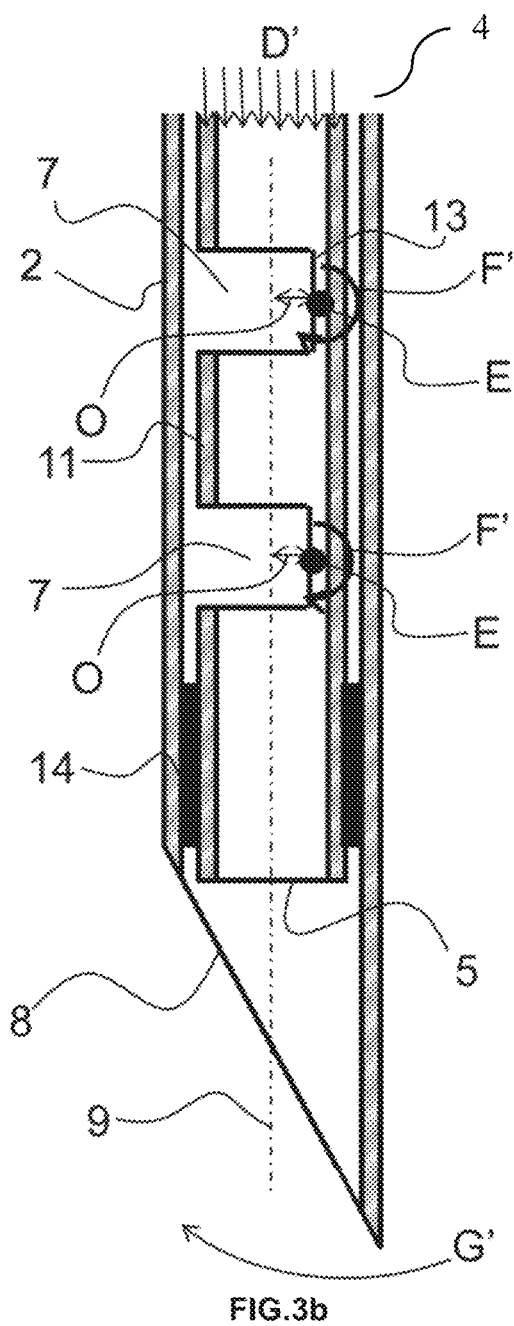
Figure 3C:
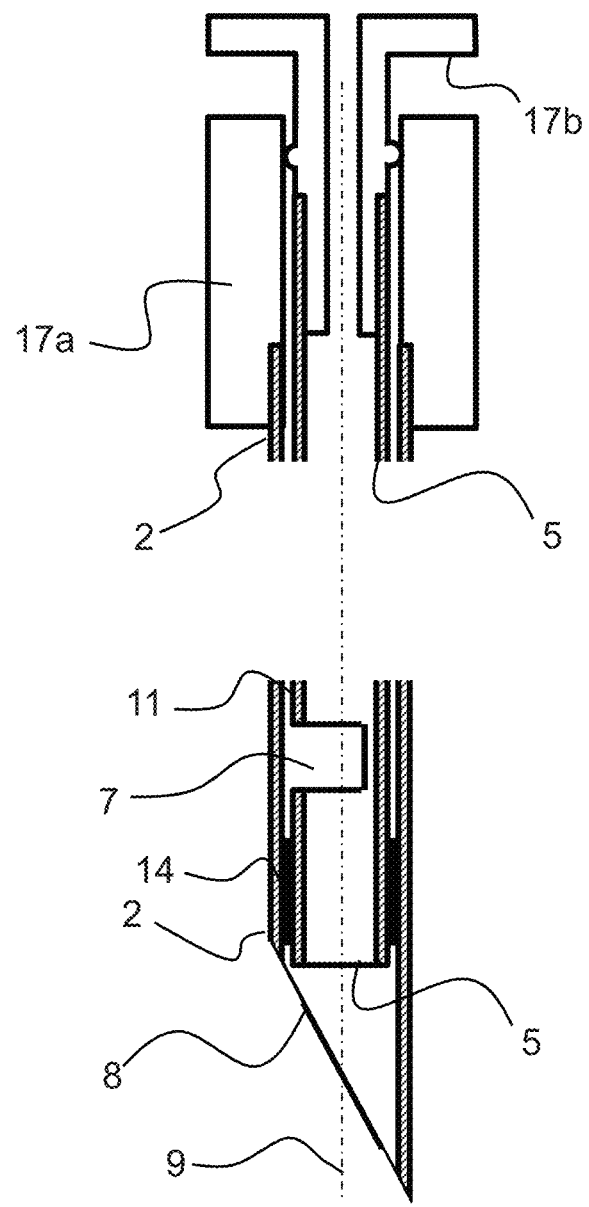
FIG. 3c is a cross sectional view of an exemplary steerable medical instrument at the distal tip and also at the handle region.

FIGS. 3a-3c illustrate the principal of steering for the steerable medical instrument 1. FIGS. 3a and 3b are the cross sectional view of the distal end 3 including centroid 9. The figures explain the conversion principal from the axial driving force D and D' to the bending moment F and F'.

In FIG. 3a, the driving tensile force D is generated by the movable parts of the handle according to operators' manipulation. The driving tensile force D is pulling the inner tube 5 from the proximal end 4, and is transmitted to the outer tube 2 via the attachment portion 14. The proximal end of the outer tube 2 is fixed on the other handle (17a in FIG. 3c). Therefore, the inner tube 5 is subjected to the tensile stress.

The tensile stress is effectively converted to bending moments F with pivots E on the position of deformable portions 13. The deformable portions 13 include offset O from centroid 9 and form moment arms for tensile stress. With these moment arms, the driving tensile force D is converted to bending moment F.

The attachment portion 14 and the rigid portion of the inner tube 11 without the openings 7 transmit the bending moment F to the outer tube. Therefore, the outer tube 2 and the inner tube 5 bend to the direction G. Since the bending moment F can be controlled by the driving tensile force D, the operators can control curvature of the steerable medical instrument 1 with the manipulation of the handle.

In FIG. 3b, the driving compression force D' is applied to the inner tube 5 by pushing the inner tube 5. In the same manner as FIG. 3a, the driving compression force is converted into the bending moment E'. The bending moment E and E' are opposite direction each other. Therefore, the outer tube 2 and the inner tube 5 bend the direction G'.

By using pull and push manipulation of the inner tube 5, the steerable medical instrument 1 can steer to both of the directions G and G'. This bidirectional operation can adjust the direction of the beveled tip 8 to the target direction if the attempt includes errors.

FIG. 3c shows the distal end of the steerable medical instrument where the movable part of the handle 17b generates the driving tensile force D as the operator manipulates the moving handle 17b, which is attached to the inner tube 5 relative to the fixed handle 17a attached to the fixed handle 17a. This tensile force D moves the inner tube 5 along the direction of the centroid 9.

Embodiment 2

Figure 4A:
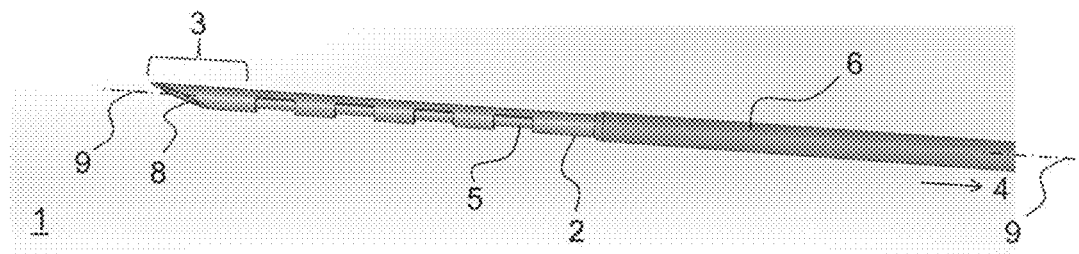
FIGS. 4a, 4b, and 4c are illustrations of an exemplary steerable medical instrument to a second embodiment of the present invention.
Figure 4B:
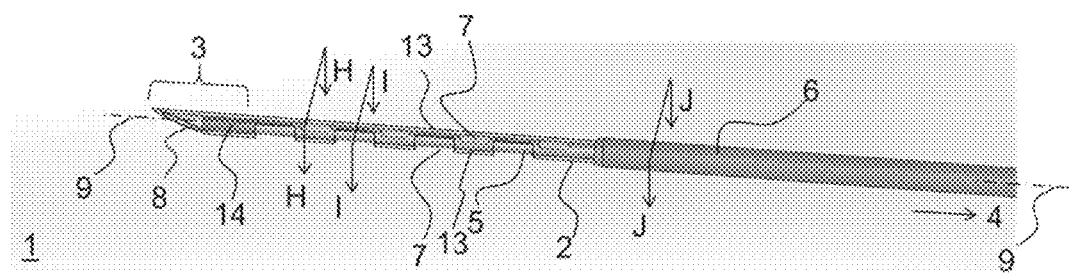
Figure 4C:
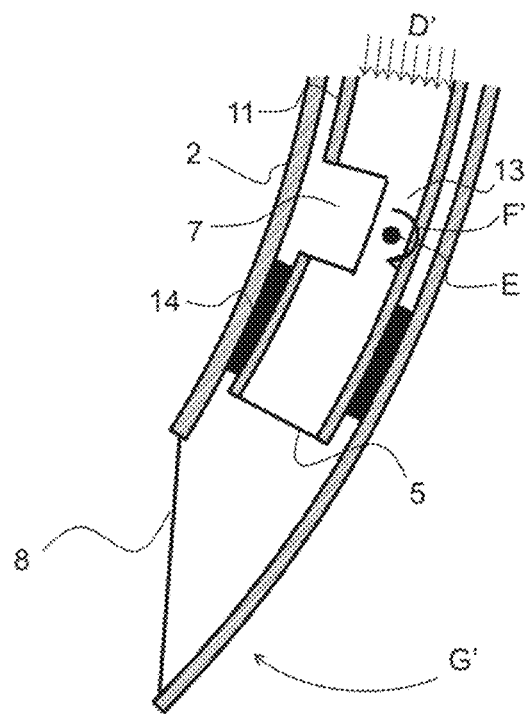

A second embodiment of the present invention has a similar configuration of the steerable medical instrument in FIGS. 1a and 1b. However, the outer tube 2 of this embodiment is different from the first embodiment. The outer tube 2 also includes openings 7 and deformable portions 13 (FIGS. 4a, 4b, 4c, 5a, 5b and 5c). Particularly, FIGS. 4a and 4b show an exemplary steerable medical instrument, where FIG. 4b shows the structure under a transparent outer tube 2 and FIG. 4c shows the probe tip when bent.

The openings 7 in the outer tube 2 are located between the adjoining openings 7 in the inner tube 5. Therefore, the outer tube 2 covers the openings 7 in the inner tube 5 while the outer tube 2 has the openings 7 at different locations. For this and some preferred embodiments, at all point along the centroid, there is preferably at least one of the outer tube 2 and inner tube 5 at all locations around the circumference of the device.

Figure 5A:
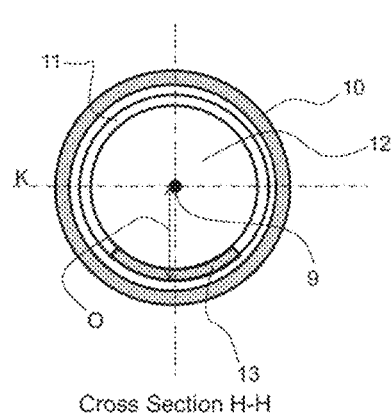
FIGS. 5a, 5b, and 5c show cross sections H-H (FIG. 5a), I-I (FIG. 5b), and J-J (FIG. 5c) as shown in FIG. 4b.
Figure 5B:
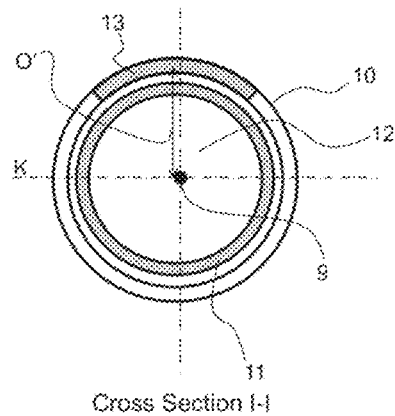
Figure 5C:
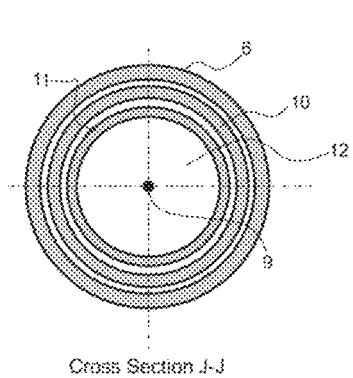

FIGS. 5a, 5b and 5c elaborate the configuration of the openings 7 and the deformable portions 13 as described in FIGS. 4a and 4b. FIG. 5a illustrates the cross sectional view of the position H-H. The opening 7 in the inner tube 5 is arranged in this position. As FIG. 5a, the deformable portion 13 with offset O from centroid 9 is formed in the inner tube 5. On the other hand, in FIG. 5b, the opening 7 in the outer tube 2 is arranged in position I-I. The deformable portion 13 with offset O' from centroid 9 is formed in the outer tube 2. These deformable portions generates the bending moment to the same directions on the outer tube 2 and the inner tube 5.

If the inner tube 5 is pulled by the handle, the inner tube 5 has the tensile stress. In opposite to this stress, the outer tube 2 is subjected to the compression stress at the same time. Since the two offset of O and O' are opposite direction against line K, these tensile and compression stresses are converted to the bending moment with the identical direction. Therefore, the axial driving force from the inner tube 5 is efficiently converted into the bending moments on both of the inner tube 5 and the outer tube 2.

Specifically, when the outer tube 2 and the inner tube 5 have effectively identical bending stiffness, the mechanical interference, for example friction force between them, can be decreased. Therefore, the steerable medical instrument 1 can reduce undesired stress concentrations from the instrument to the anatomy since the steerable medical instrument 1 bend with constant curvature. Moreover, the axial driving force can be used for bending moment without loss for friction force.

The channel 12 is isolated from the outside of the steerable medical instrument 1 through all length of the steerable medical instrument 1. As FIGS. 5a, 5b and 5c, ether the inner-tube, the outer-tube or the introducer walls isolate the channel 12 from outside in any positions in the instrument.

Embodiment 3

A third embodiment of the present invention has a similar configuration of the steerable medical instrument in FIGS. 1a and 1b. However, the inner tube 5 is different from the first embodiment.

Figure 6A:
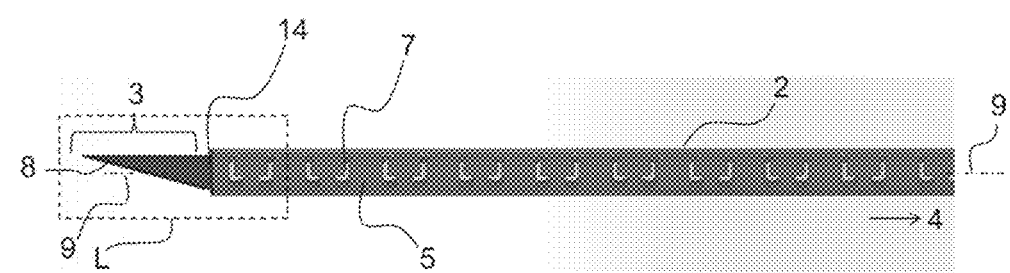
FIGS. 6a-6c.

The side view of the steerable medical instrument 1 is shown in FIG. 6a. The inner tube 5 includes the beveled tip 8 at the distal end 3. The outer tube is terminated before the beveled tip 8 and is attached via the attachment portion 14 on the inner tube 2. With this configuration, a flexible and thin tube can be used for the outer tube 2 because the outer tube 2 does not need the beveled tip 8 to puncture the anatomy. The outer tube 2 is predominant in bending rigidity of the steerable medical instrument 1. Therefore, more flexible instrument can be developed.

Figure 6B:
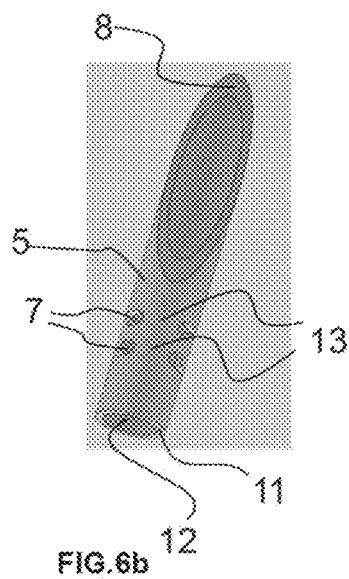
Figure 6C:
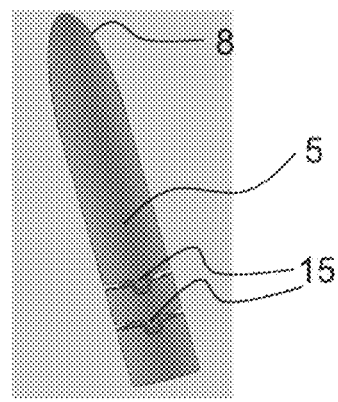

In this embodiment, the inner tube 5 also includes a plurality of key portions 15 on the opposite side from the deformable portions 13. FIGS. 6b and 6c are closed-up view of the box L with dotted lines. The openings 7 form key portions 15 as well as the deformable portions 13. The key portions 15 provide a means to limit torsional motion and out-of-plane motion from a designed bending plane, and make the bending stay on the designed bending plane reducing error of direction of the needle insertion. Also, the key portions 15 can be used to limit maximum bending angle of deformable portions 13. Therefore, the key portions 15 can decrease risks of breaking the instrument.

Figure 7A:
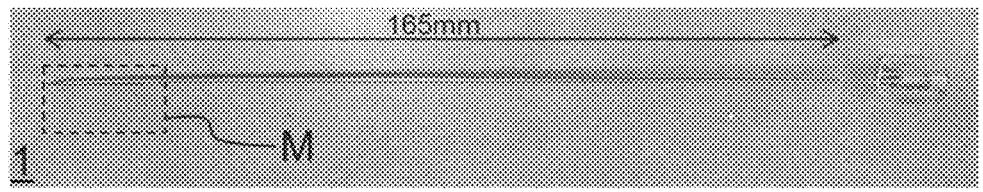
Figure 7B:
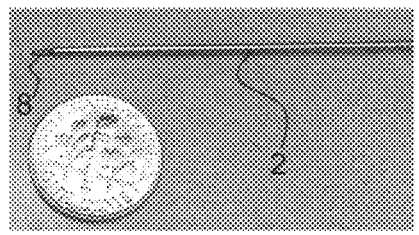
Figures 8A, 8B, 8C, 8D:
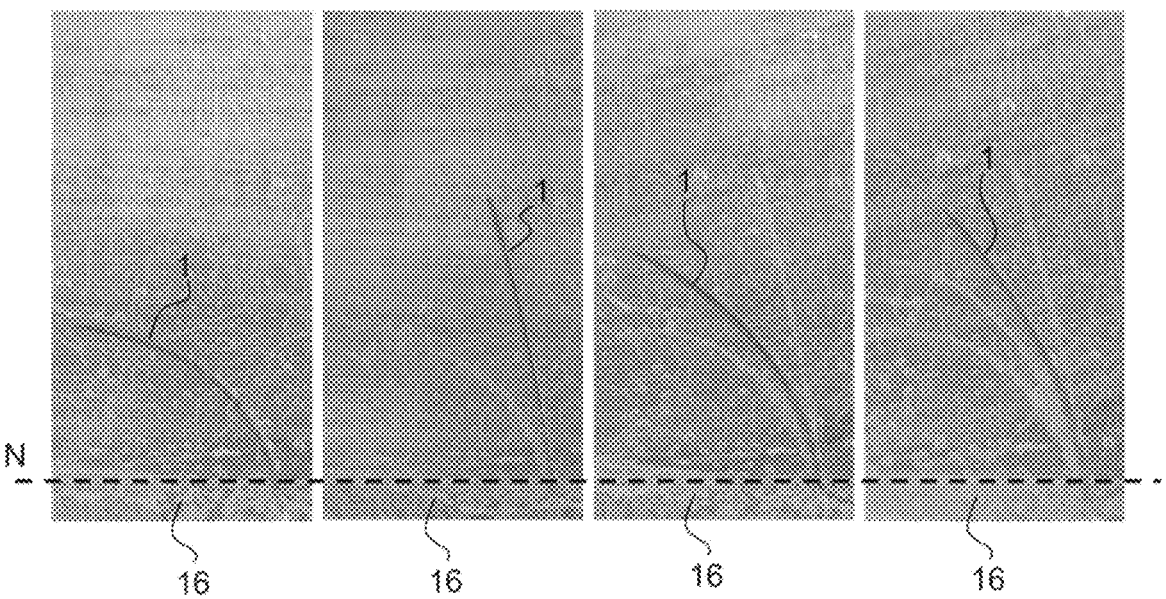
FIGS. 8a-8d are each images of an exemplary steerable medical instrument during an insertion test.

An exemplary steerable medical instrument 1 is shown in FIGS. 7a and 7b. In one exemplary embodiment, the inner tube 5 was made of super elastic Ni—Ti alloy tube. The openings 7 were created with laser-cutting technique. The outer and inner diameters of the inner tube 5 were 0.036" (0.91 mm) and 0.024" (0.61). The outer tube 2 was helical hollow strand (HHS tube by Fort Wayne Metal Inc.). The outer and inner diameters were 0.048" (1.22 mm) and 0.041" (1.04 mm). The effective insertion length is around 165 mm.

FIGS. 8a-8d demonstrate the insertion characteristics in an insertion test with this exemplary embodiment of the steerable medical device. This medical device was inserted into a phantom with four different curvatures with its insertion depth of around 30 mm. The needle was injected from the guide hole on the container wall 16. The container was filled with a gel-like wax as a phantom. A boundary between the gel-like wax and the container wall 16 is shown as the dotted line N. The curvature control was performed by manual operation. The exemplary steerable medical instrument 1 was successfully inserted with four different curvatures by modifying the curvature of the inner tube 2. The minimum curvature radius was around 21 mm for the 30-mm insertion. The rupture of the phantom was not observed in any insertion. Additionally, after the placement as imaged in FIGS. 8a-8d, the exemplary steerable medical instrument was removed from the phantom along the curved path without the rupture of the phantom.

Additional Embodiments

In some exemplary embodiments, the tip of the steerable medical instrument can be articulated by controlling the position of the inner tube so that physician can adjust the insertion direction or the tip position/direction after insertion without reinsertion. Therefore, the needle placement accuracy can be improved without increasing the number of attempted insertions. Maintaining a single or low number of insertions is important for reducing the risks of seeding cancer along the insertion trajectory during biopsy and ablation therapy. Thus, these embodiments provide a particular advantage in providing more accurate insertion direction and position without the need for additional insertions.

In some exemplary embodiments, the steerable medical instrument has hollow portion so that physicians can use it as one or more tool channels to include various medical devices, for example ablation applicators, tracking sensors and endoscopes, or channel to suction/injection any liquid or tissues. The device may include 1, 2 or more separate hollow portions that allow for a variety of tools—inserted either simultaneously or sequentially or suction/injection channels. Therefore, the steerable medical instrument as described herein can form a functional medical device without any additional parts or insertion procedures. Consequently, the instrument can reduce complexity of many procedures and provides a particular advantage in its use.

In yet other exemplary embodiments, the opening in the outer-tube and/or the inner tube forms the deformable portion which is offset from the centroid. The deformable portion with the offset can transform the axial driving force along longitudinal direction from the inner-tube into the bending moment to steer the instrument with minimal structure. Therefore, the steerable medical instrument can be miniaturized into the sufficient needle gauge for medical application.

In some exemplary embodiments, the only openings are located on the inner tube. These embodiments allow the steerable medical instrument avoid exposing the deformable portion to an interface between the instrument and the anatomy during the insertion. Therefore, this configuration makes the fragile structure away from the high stress from anatomy. Moreover, this configuration can hide the openings that include edges of the walls from the anatomy so that the steerable medical instrument can avoid risks to harm the anatomy with these edges. This configuration may also provide the advantage of increased ability to sterilize the instrument since there are not openings that may not be easily cleaned on the outer portion of the instrument.

In some exemplary embodiments, there are openings on the inner-tube and on the outer-tube. This allows the steerable medical instrument to be able to bend at larger curvature with small input tension. Therefore, the steerable medical instrument of these embodiments can be used to explore in more confined spaces and can reduce to the tension applied on the fixing spot of the inner tube on the outer tube compared to other instruments so as to reduce the change of breakage at the fixing spot.

In yet other exemplary embodiments, the openings are in the outer-tube and the inner-tube where the opening location alternates between the inner and outer tubes. Thus, the steerable medical instrument of these embodiments can form a continuous wall to seal inside of the instrument from outside of the instruments. Therefore the steerable medical instrument of these embodiments can be used as diagnostic or therapeutic sheaths or needles without any additional jacket outside the instrument.

Moreover, in some embodiments, the deformable portions can be distributed evenly along longitudinal directions. Therefore, the steerable medical instrument can be bent with constant curvature. The constant curvature leads to avoid stress concentration to the anatomy on the spot with an uneven large curvature.

In some exemplary embodiments, the deformable portions on the outer-tube and the inner-tube are arranged with an antagonistic geometry. For example, the outer-tube and the inner-tube can include openings 7 in their deformable portions at the opposite direction each other (FIGS. 4a and 4b). With this configuration, the offsets O extend to the opposite direction from centroid 9 in the outer- and the inner- tubes. Therefore, in both the outer- and the inner-tubes, the bending moments at the same direction of bending can be generated. Thus, the bending moments on the outer-tube and the inner-tube can be aligned to the same bending direction. Therefore, with this configuration, the driving force can be more effectively used for bending of the steerable instrument.

In yet other exemplary embodiments, the deformable portions are distributed along direction of the centroid. In these embodiments, buckling of deformable portions can be reduced or avoided when the driving force is a compression force, because aspect ratio of one plural deformable portion is reduced as depicted in FIGS. 4b and 4c. Therefore, bidirectional steering control by using a push and pull manipulation of the inner tube can be achieved. Also large bending curvature and/or actuation of stiff instruments can be achieved with the driving compression force without buckling. Also low aspect ratio of the deformable portions makes the deformable portions rigid to torsional motions. Therefore, undesired torsional motion accompanying to steering motion can be reduced. In embodiments having a key portion 15, the key portion can provide the means to avoid the undesired torsional motion of the deformable portions. Therefore, the instrument can achieve improved positioning accuracy and predictable bending motions.

In some exemplary embodiments, the outer and inner tubes effectively have identical or almost identical bending stiffnesses. Thus, the steerable medical instrument of these embodiments has reduced the mechanical interaction. For example, normal force between two walls and friction force between them, when the instrument bends. Therefore, the instrument can reduce the driving tension for bending and achieve a constant curvature. The reduction of the driving tension has the particular advantage of avoiding or reducing risks of breaking the steerable medical instruments, improving usability of physicians, and simplifying and miniaturizing the structure to actuate the inner tube. Moreover, constant curvature can avoid stress concentration to the anatomy on the spot with an uneven large curvature.

In yet other exemplary embodiments, the introducer is on the most outside of the instrument; the outer tube with the inner tube can easily turn without interaction to the anatomy after the insertion. Therefore, in these embodiments, the physician can choose the insertion direction without harming the anatomy. Moreover, the introducer reduces any physical interaction in a case of multiple insertions. Therefore, physician can target multiple spots by using steerable functions of the instruments without repetition of difficult needle placement or multiple punctures through the skin and additional risks of seeding of cancer or harming of the anatomy.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The comparative term, the same, as used herein, means that the two values are within 10% or more preferably within 5% of each other.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Exemplary embodiments will be described below with reference to the several drawings, wherein like reference numerals designate identical or corresponding parts throughout the several views and embodiments. Accordingly, descriptions of such parts with like reference numerals will not be repeated with respect to multiple figures.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A steerable medical instrument comprising:
    an outer tube having a centroid along the longitudinal direction and having a proximal and a distal end; and
    an inner tube having a centroid along the longitudinal direction and having a proximal and a distal end, which is surrounded by the outer tube,
    wherein the inner tube is movable along the direction of the centroid at the proximal end, and the inner tube is fixed at the distal end to the distal end of the outer tube,
    wherein at least one of the outer tube and inner tube has a plurality of openings, which creates deformable portions with offset from the centroid so that the outer and the inner tubes can bend by moving the inner tube at the proximal end, and
    wherein the outer tube and inner tube have effectively the same bending stiffness, and wherein the inner tube has a beveled tip to puncture an anatomy.

2. The steerable medical instrument according to claim 1, wherein both the outer tube and the inner tube have the plurality of openings.

3. The steerable medical instrument according to claim 1, wherein a plurality of deformable portions are distributed along the centroid axis.

4. The steerable medical instrument according to claim 1, wherein the plurality of openings are configured to have key portions that limit torsional motion of the steerable medical instrument.

5. The steerable medical instrument according to claim 1, wherein the steerable medical instrument has an introducer, which locates outside of the outer tube sharing the centroid, wherein the outer tube is rotatable within the introducer.

6. The steerable medical instrument according to claim 1, wherein the plurality of opening each span at least ⅛ of the circumference of the tube having the plurality of openings.

7. The steerable medical instrument according to claim 1, wherein the plurality of openings are "L" or "J" shaped when viewed in circular cross-section, running perpendicular to the centroid.

8. The steerable medical instrument according to claim 1, wherein there is at least one opening per length L, where L is three time the diameter of the outer tube.

9. The steerable medical instrument according to claim 1, wherein the plurality of openings form a regular pattern.

10. A steerable medical instrument comprising:
    an outer tube having a centroid along longitudinal direction and having a proximal and a distal end and having a plurality of openings, an inner tube having a centroid along longitudinal direction and having a proximal and a distal end, which is surrounded by the outer tube and having a plurality of openings, wherein the inner tube is movable along the direction of the centroid at the proximal end, and the inner tube is fixed at the distal end to the distal end of the outer tube, and the outer and the inner tubes can bend by moving the inner tube at the proximal end, and wherein the plurality of openings in the outer tube and the inner tube are deployed alternately between the outer tube and the inner tube along the longitudinal direction, and wherein the outer tube and inner tube have effectively the same bending stiffness, and wherein the inner tube has a beveled tip to puncture an anatomy.

11. A bendable tubular body comprising:

an outer tube having a centroid along longitudinal direction and having a proximal and a distal end; and an inner tube having a centroid along longitudinal direction and having a proximal and a distal end, which is surrounded by the outer tube, wherein the inner tube is movable along the direction of the centroid at the proximal end, and the inner tube is fixed at the distal end to the outer tube, and wherein at least one of the outer and the inner tubes have a plurality of openings, which creates effective deformable portions with offset from the centroid so that the outer and the inner tubes can bend by moving the inner tube at the proximal end, wherein the inner tube and outer tube together form a bendable tubular body with limited torsional motion, and wherein the outer tube and inner tube have effectively the same bending stiffness, and wherein the inner tube has a beveled tip to puncture an anatomy.

12. The steerable medical instrument according to claim 1, wherein the plurality of openings are configured to have a low aspect ratio of openings that limits torsional motion of the steerable medical instrument.

13. The steerable medical instrument according to claim 1, wherein the plurality of openings are configured such that the inner tube and outer tube form a continuous wall to seal an inside of the steerable medical instrument from an outside of the steerable medical instrument.

14. The steerable medical instrument according to claim 1, wherein only the inner tube as the plurality of openings.

15. The steerable medical instrument according to claim 2, wherein the deformable portions of the outer tube and the deformable portions of the inner tube have an antagonistic geometry.

16. The steerable medical instrument according to claim 2, the plurality of openings in the outer tube and the inner tube are deployed alternately between the outer tube and the inner tube along a longitudinal direction and are not overlaid on each other.

* * * * *